US009132244B2

(12) United States Patent
Dyche et al.

(10) Patent No.: US 9,132,244 B2
(45) Date of Patent: Sep. 15, 2015

(54) MEDICATION DELIVERY APPARATUS INCLUDING A MEDICATION METERING SYSTEM

(75) Inventors: Anthony Dyche, Hayling Island (GB); Ian Thomas Petherbridge, Bognor Regis (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 663 days.

(21) Appl. No.: 13/503,718

(22) PCT Filed: Oct. 4, 2010

(86) PCT No.: PCT/IB2010/054471

§ 371 (c)(1), (2), (4) Date: Apr. 24, 2012

(87) PCT Pub. No.: WO2011/055243

PCT Pub. Date: May 12, 2011

(65) Prior Publication Data

US 2012/0216800 A1 Aug. 30, 2012

Related U.S. Application Data

(60) Provisional application No. 61/257,867, filed on Nov. 4, 2009.

(51) Int. Cl.
*A61M 11/00* (2006.01)
*B05B 17/06* (2006.01)
(Continued)

(52) U.S. Cl.
CPC ........... *A61M 11/005* (2013.01); *A61M 11/007* (2014.02); *A61M 15/0066* (2014.02); *B05B 17/0623* (2013.01); *B05B 17/0638* (2013.01); *A61M 2205/8206* (2013.01)

(58) Field of Classification Search
CPC .......... A61M 11/005; A61M 15/0066; A61M 11/007; A61M 15/00; A61M 15/0065; A61M 15/0085; A61M 15/0028; A61M 15/025; B05B 17/0638; B05B 17/0623; B05B 11/02; B05B 17/06; B05B 11/06; B05B 17/0646; B05B 11/309; B05B 11/3094; B05B 12/08; B05B 17/0684; G01F 11/32; B65D 83/60; B41J 2/025; C25D 1/08
USPC ............. 128/200.11–200.24, 203.12, 203.15, 128/205.24; 222/319, 145.5, 631, 357; 239/338; 261/DIG. 48
See application file for complete search history.

(56) References Cited

U.S. PATENT DOCUMENTS 3,666,150 A 5/1972 Liljeholm
5,515,842 A * 5/1996 Ramseyer et al. ....... 128/200.18
(Continued)

FOREIGN PATENT DOCUMENTS

GB 1568888 6/1980
GB 2272389 A 5/1994
(Continued)

*Primary Examiner* — Annette Dixon
(74) *Attorney, Agent, or Firm* — Michael W. Haas

(57) ABSTRACT

A medication delivery apparatus (5) includes a reservoir for holding a liquid medication and a metering device (25) coupled to the reservoir for supplying a dose of the liquid medication to the reservoir. The metering device includes an upper chamber, a lower chamber coupled to the upper chamber, a piston selectively moveable within the upper chamber and the lower chamber and a valve providing selective fluid communication between the lower chamber and the reservoir in response to movement of the piston.

26 Claims, 4 Drawing Sheets

(51) Int. Cl.
*B05B 17/00* (2006.01)
*A61M 15/00* (2006.01)

(56) References Cited

U.S. PATENT DOCUMENTS

| | | | | |
|---|---|---|---|---|
| 5,876,189 | A | | 3/1999 | Lukas et al. |
| 5,950,619 | A | * | 9/1999 | van der Linden et al. ........................ 128/200.16 |
| 5,970,974 | A | * | 10/1999 | Van Der Linden et al. ........................ 128/200.16 |
| 6,675,845 | B2 | | 1/2004 | Volpenheim et al. |
| 7,168,597 | B1 | | 1/2007 | Jones et al. |
| 2003/0146300 | A1 | | 8/2003 | Denyer et al. |
| 2004/0139963 | A1 | | 7/2004 | Ivri et al. |
| 2007/0145077 | A1 | | 6/2007 | Harrold |
| 2007/0219496 | A1 | | 9/2007 | Kamen et al. |
| 2008/0078783 | A1 | | 4/2008 | Helmlinger |

FOREIGN PATENT DOCUMENTS

| | | | |
|---|---|---|---|
| GB | 2384198 | A | 7/2003 |
| JP | 2005066187 | A | 3/2005 |
| JP | 2008089181 | A | 4/2008 |
| JP | 2009521673 | A | 6/2009 |
| WO | 02074443 | A2 | 9/2002 |

* cited by examiner

MEDICATION DELIVERY APPARATUS INCLUDING A MEDICATION METERING SYSTEM

The present invention relates to medication delivery apparatus, such as nebulizers, and in particular, to a medication delivery apparatus having a metering system for controlling the amount of medication that is provided for delivery to a patient.

BACKGROUND OF THE INVENTION

1. Field of the Invention

A number of devices are available for delivering a drug into the lungs of a patient. Once such device is a nebulizer, which is a device that is used for converting a liquid, such as a liquid medication, into an aerosol which is then inhaled by the patient, typically through a mouthpiece. A number of different types of nebulizers exist, such as, without limitation, jet nebulizers (sometimes referred to as pneumatic nebulizers) and ultrasonic nebulizers. A typical jet nebulizer uses compressed air to generate the aerosol from the liquid. One type of ultrasonic nebulizer employs acoustic waves having an ultrasonic frequency that are directed to a point on the surface of the liquid that is to be converted into an aerosol. At the point on the surface of the liquid where these ultrasonic waves converge, they will produce capillary waves that oscillate at the frequency of the ultrasonic waves. If the amplitude of the waves is large enough, the peaks of the capillary waves will break away from the liquid and be ejected from the surface of the liquid in the form of droplets, thereby forming the aerosol. A device that is often used for generating ultrasonic waves in an ultrasonic nebulizer is a piezoelectric transducer (such as a piezoelectric crystal), which vibrates and generates ultrasonic waves in response to an applied electric field. In another type of ultrasonic nebulizer, the liquid that is to be converted into an aerosol is forced through a mesh (thereby creating liquid droplets) by the vibration of a piezoelectric crystal acting upon a horn. In this type of ultrasonic nebulizer, typically referred to as a mesh nebulizer, the gauge of the mesh determines the size of the droplets which are created to form the aerosol.

2. Description of the Related Art

Conventional nebulizer systems provide a continuous aerosol/drug output, and thus the amount of drug inhaled is dependent upon the patient's breathing pattern. The duty cycle of the patient's breathing pattern is typically 40:60. This means that the patient spends 40 percent of a single respiratory cycle in inspiration and 60 percent of the time in expiration. Thus, 60 percent of the drug delivered from the nebulizer will be wasted to the environment during expiration. In addition, the breathing pattern of a single patient over the course of a treatment will vary.

In order to address these issues, more sophisticated nebulizer systems, referred to as adaptive nebulizer systems based on what is known as Adaptive Aerosol Delivery (AAD) technology, have been developed which adapt the delivery of aerosol to the patient's breathing pattern, delivering medication only when the patient is inhaling through the mouthpiece. Because adaptive nebulizer systems are able to deliver the medication very efficiently (nearly all of the medication supplied to the nebulizer is actually delivered to the patient), it is important that the amount of medication supplied to the nebulizer be as precise as possible so that the patient will receive the correct dose.

In one known method of controlling the volume of medication, a syringe is used to draw a precise amount of medication from a vial, and the drawn medication is then transferred to a chamber in the nebulizer. This method has a number of disadvantages. For example, patients with poor dexterity, such as the elderly, may find it difficult to use a syringe in this manner Also, the use of syringes presents the danger of needle-stick injuries, and sharps containers are required for disposal. Syringes also present an additional part that the patient must keep track of and carry with them when they leave their home.

CROSS-REFERENCE TO RELATED APPLICATIONS

United States Patent Application Publication Number 2003/0146300, owned by the assignee of the present invention, describes a nebulizer that includes a nebulization device for nebulizing a medication and a reservoir having a metering chamber arranged so as to feed the medication to the nebulization device and a second chamber arranged to hold and retain any of the medication that is in excess of the volume held in the metering chamber. While this approach is effective for certain applications, there is room for improvement in the area of nebulizers and methods for controlling the amount of medication delivered to the patient.

SUMMARY OF THE INVENTION

In one embodiment, a medication delivery apparatus is provided that includes a reservoir for holding a liquid medication and a metering device coupled to the reservoir for supplying a dose of the liquid medication to the reservoir. The metering device includes an upper chamber, a lower chamber coupled to the upper chamber, a piston, the piston being selectively moveable within the upper chamber and the lower chamber along a longitudinal axis of the upper chamber and the lower chamber, and a valve, the valve providing selective fluid communication between the lower chamber and the reservoir in response to movement of the piston. In one specific embodiment, the valve is a one-way valve (such as a duck-bill valve), wherein the valve is biased to be in a normally closed condition wherein the lower chamber is not in fluid communication with the reservoir and is structured to move to an open condition wherein the lower chamber is in fluid communication with the reservoir in response to a force being applied to the valve as a result of the piston moving toward the valve within the lower chamber.

In another particular embodiment, the lower chamber and the upper chamber are each cylindrical in shape, and the bore of the upper chamber is greater than the bore of the lower chamber. Also, the piston may include a cylindrical bottom end having a seal element coupled thereto, the seal element being structured to engage the inner wall of the lower chamber when the piston moves within the lower chamber.

In another particular embodiment, the piston is part of a cap that is structured to be selectively coupled to the upper chamber. When the cap is coupled to the upper chamber, the cap may be structured to be rotatable relative to the upper chamber, wherein rotation of the cap causes the piston to move within the lower chamber. In this embodiment, the upper chamber may include a pin on the outer wall thereof, wherein the cap includes an angled thread (such as a quarter turn thread), wherein the pin is structured to engage the thread when the cap is coupled to the upper chamber.

In a different embodiment, when the cap is coupled to the upper chamber, the cap is structured to be movable relative to the upper chamber downwardly and along the longitudinal axis of the upper chamber, wherein movement of the cap causes the piston to move within the lower chamber.

The piston may include a central bore and a second valve in the central bore, wherein the central bore is vented to atmosphere through a hole provided in the cap.

The medication delivery apparatus may further include one or more additional caps that may be selectively coupled to the upper chamber, each of the one or more additional caps having an associated piston that is different than the piston of the cap. The piston of the cap may have a first stroke, and one or more of the one or more additional caps each may have an associated piston having an associated stroke that is different than the first stroke. The apparatus may further include an insert structured to be received with the lower chamber, the lower chamber having a first bore and the insert having a second bore that is smaller than the first bore, wherein one of the one or more additional caps has an associated piston that is sized and structured for use with the insert.

The medication delivery apparatus may be a nebulizer, wherein the reservoir is part of an aerosol generation system, and wherein the reservoir holds the dose of the liquid medication to enable the dose of the liquid medication to be nebulized by the aerosol generation system for delivery to a patient.

In another embodiment, a method of providing a dose of a liquid medication to a reservoir of a medication delivery apparatus is provided that includes supplying an amount of the liquid medication to an upper chamber and a lower chamber of a metering device, the amount being larger than the dose, the lower chamber being coupled to the upper chamber, a first portion of the amount being held in the lower chamber and a second portion of the amount being held in the upper chamber, wherein the lower chamber is not in fluid communication with the reservoir under a static pressure of the first portion in the lower chamber, and applying a force to the first portion in the lower chamber through the upper chamber, the force causing at least a part of the first portion to exit the lower chamber and be received in the reservoir of the medication delivery apparatus, the second portion being maintained within the metering device after application of the force.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
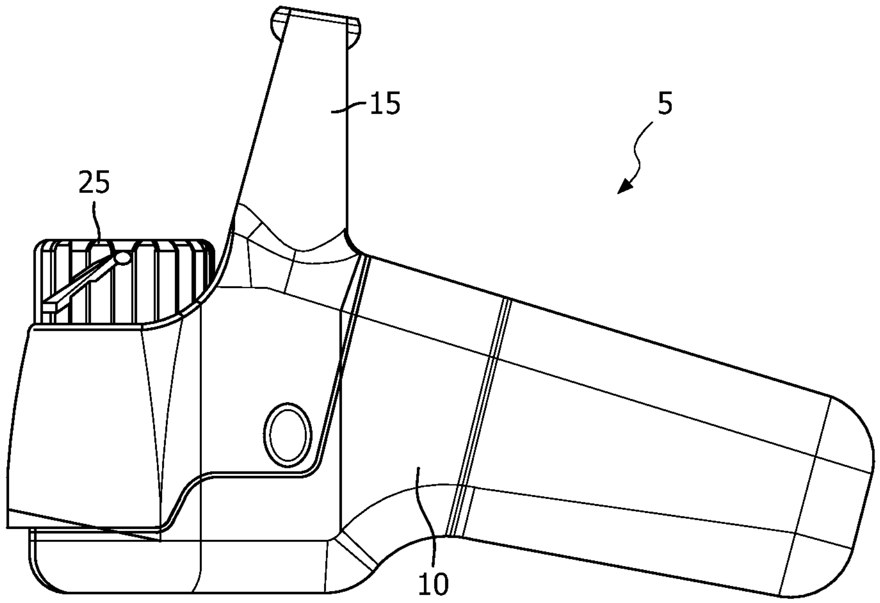
FIG. 1 is a side elevational view.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

DETAILED DESCRIPTION OF EXEMPLARY EMBOIDMENTS

Figure 2:
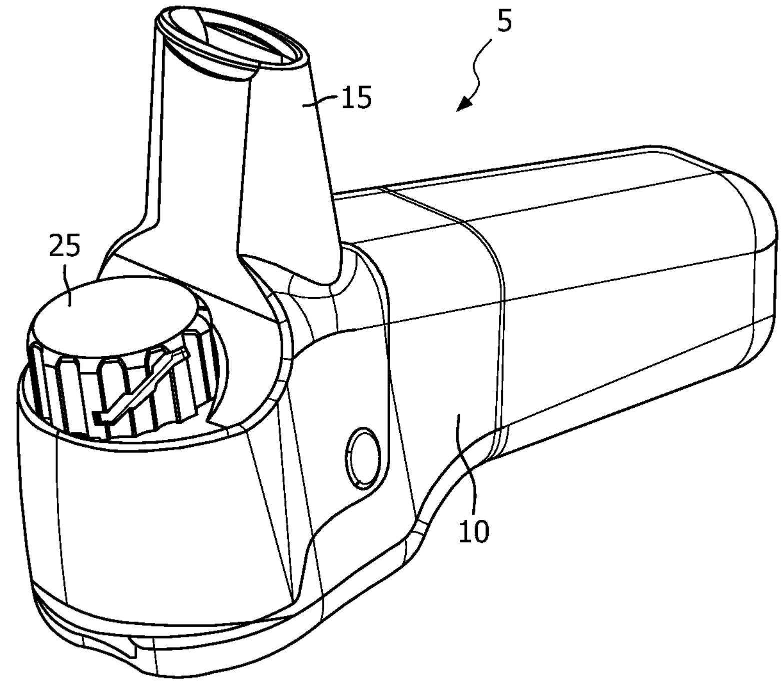
FIG. 2 is an isometric view of nebulizer device according to one embodiment of the invention.
Figure 3:
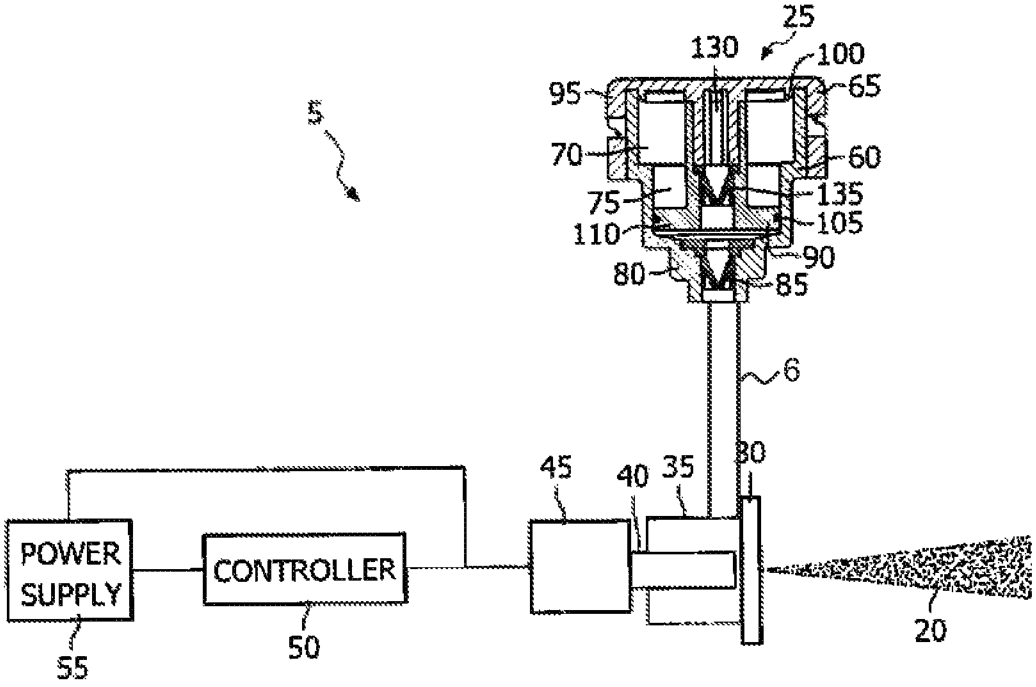
FIG. 3 is a schematic diagram of the nebulizer device of FIGS. 1 and 2 which shows selected components thereof in a simplified or symbolic form.

FIG. 1 is a side elevational view and FIG. 2 is an isometric view of nebulizer device 5 according to one embodiment of the invention. FIG. 3 is a schematic diagram of nebulizer device 5 which shows selected components thereof in a simplified or symbolic form. Nebulizer device 5 functions as a drug delivery system for delivering a drug in the form of aerosol 20 (FIG. 3) into the lungs of a patient. Nebulizer device 5 includes main housing 10 which houses certain components (shown in FIG. 3 and described below) of nebulizer device 5 and mouthpiece portion 15 which is in the illustrated embodiment removeably attached to the main housing 10. Nebulizer device 5 also includes metering device 25, described in greater detail below, which is structured to control the amount of medication that is supplied to the internal components of nebulizer 5 for conversion into aerosol 20 and ultimately delivery to the patient. The mouthpiece portion 15 is structured to be received in the mouth of the patient and includes a chamber which, when the mouthpiece portion 15 is attached to the main housing 10, is structured to receive the aerosol 20 that is generated by the components in the main housing 10 as described in more detail below. When the patient places his or her mouth on the end of the mouthpiece portion 15 and inhales, an air stream is created that carries the aerosol 20 into the lungs of the patient.

As seen in FIG. 3, nebulizer 5 includes mesh plate 30 (including a plurality of miniature holes therein), reservoir 35 for holding the liquid (drug) to be converted into aerosol 20, horn 40, and piezoelectric transducer 45 operatively coupled to horn 40. Metering device 25 is in fluid communication with reservoir 35, as indicated by pathway 6, and, as described in greater detail herein, is structured to deliver a controlled volume of liquid to reservoir 35 for conversion into aerosol 20. Nebulizer 5 also includes controller 50, which may be a microprocessor, microcontroller, or some other suitable electronic control device or circuitry, and power supply 55, which may be a rechargeable battery. Horn 40 is located close to the rear face of mesh plate 30 and may be caused to vibrate by piezoelectric transducer 45 under the control of controller 50, with the power to drive piezoelectric transducer 45 being provided by power supply 55. The liquid in reservoir 35 is in fluid contact with the rear face of the mesh plate 30. When piezoelectric transducer 45 is caused to vibrate, it drives horn 40 to vibrate in the region of mesh plate 30. As a result of such vibration of horn 40, the liquid from reservoir 35 is forced through the holes of mesh plate 30, thereby generating aerosol 20 (in the form of a plume) that is injected into mouthpiece portion 15.

It should be understood that the mesh plate type aerosol generation system shown in FIG. 3 and just described is meant to be exemplary and is just one type of aerosol generation system that may be employed in connection with the present invention. It is contemplated that others type of aerosol generation systems may be employed within the scope of the present invention. For example, and without limitation, an aerosol generation system that employs a piezeo element around the outside of the mesh and not a separate horn as in FIG. 3 may be employed. As another non-limiting example, a pneumatic type aerosol generation system may be employed.

Figure 4:
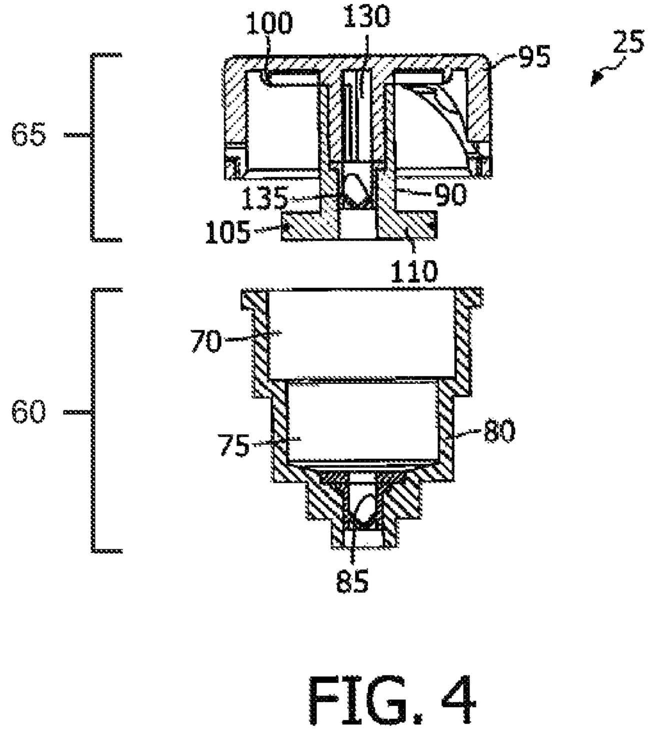
FIG. 4 is a cross-sectional view and FIG. 5 is a front elevational view of a metering device according to one particular embodiment.
Figure 5:
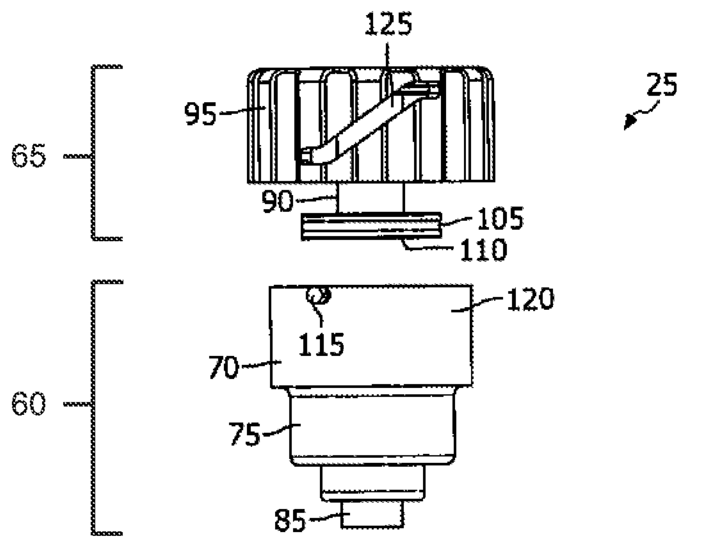

FIG. 4 is a cross-sectional view and FIG. 5 is a front elevational view of metering device 25 according to one particular embodiment. Metering device 25 includes metering chamber 60 and cap 65. Metering chamber 60 includes upper cylindrical chamber 70, lower cylindrical chamber 75, and port portion 80. As seen in FIGS. 3 to 5, the bore (i.e., inner diameter) of upper cylindrical chamber 70 is larger that the bore (i.e., inner diameter) of lower cylindrical chamber 75. In an exemplary embodiment, metering chamber 60 is provided within main housing 10 of nebulizer 5 and metering device 25 is provided as an integral part of nebulizer 5 (see FIGS. 1 and 2). Alternatively, metering device 25 may be detachable and selectively coupled to reservoir 35. In either case, port portion 80 is structured to be in fluid communication with reservoir 35 and includes internal one-way valve 85, which in the embodiment shown is a rubber duck-bill valve. Cap 65 includes internal piston 90, outer wall 95 and sealing lip 100. Piston 90 is provided with sealing element 105, which in the illustrated embodiment is in the form of an O-ring, at cylindrical bottom end 110 of piston 90. In addition, pin 115 is provided on outer wall 120 of upper cylindrical chamber 70 of metering chamber 60, and angled quarter turn thread 125 is provided within outer wall 95 of cap 65, and is structured to receive pin 115.

In the particular embodiment where the one-way valve 85 is a rubber duck-bill valve, for the normal installation of the one-way valve 85, a 10-15% axial compression of the flange is necessary with OD clearance to permit radial deformation. For proper function there should also be a small clearance around the barrel (cylindrical portion) of the one-way valve 85. This ensures the valve normally requires a forward opening pressure to open the valve where 1 mbar is equivalent to 10 mmWG. In addition, to ensure the valve opening pressure is greater than the height of the metering chamber 60, the flange of the one-way valve 85 can be installed in an elliptical socket. If the flange is compressed along the axis of the duck-bill, then the load will cause the valve 85 to open. However, if the pressure is applied perpendicular to the axis of the duck-bill, then the load will stretch the duck bill and increase the opening pressures.

In operation, a vial containing liquid medication is emptied into metering chamber 60 where it fills both lower cylindrical chamber 75 and overflows into upper cylindrical chamber 70. The liquid medication is prevented from leaving the bottom of lower cylindrical chamber 75 by one-way valve 85. The volume of the liquid medication to be metered is substantially determined by the volume of lower cylindrical chamber 75 and the stroke of the piston 90. Depending on the viscosity of the liquid it may also fill the one-way valve 85. However the volume of space within the one-way valve 85 is small enough to not have a great effect on the overall dose tolerance.

Cap 65 is then attached to metering chamber 60. In particular, piston 90 is inserted into metering chamber 60 and pin 115 is received within and engages quarter turn thread 125.

Cap 65 is then moved in a one quarter turn. During this turn, cap 65 is guided and limited by the movement of quarter turn thread 125 over pin 115. Also during this turn, seal element 105 engages with the inner wall surface of lower cylindrical chamber 75 and provides a seal. This quarter turn of cap 65 drives bottom end 110 of piston 90 from the top to the bottom of lower cylindrical chamber 75. This movement delivers the metered volume of the liquid medication from lower cylindrical chamber 75 through port portion 80 and valve 85 (pressure from piston 90 causes valve 85 to open) to reservoir 35 of the mesh aerosol generation system of nebulizer 5. More specifically, valve 85 is biased to be normally in a closed condition (under the static pressure of the liquid in the lower cylindrical chamber 75) wherein lower cylindrical chamber 75 is not in fluid communication with reservoir 35 and is structured to move to an open condition wherein lower cylindrical chamber 75 is in fluid communication with reservoir 35 in response to a force being applied to the liquid in lower cylindrical chamber 75 and valve 85 as a result of piston 90 moving toward valve 85 within lower cylindrical chamber 75. Any residual liquid will be contained in the lower cylindrical chamber 75 above bottom end 110 of piston 90 and the seal created by seal element 105.

Cap 65 may be removed by moving it a quarter turn in the opposite direction. Piston 90 includes a central bore 130 having a second one-way valve 135, which in the illustrated embodiment is a rubber duck-bill valve, which allows cap 65 to be removed from metering chamber 60 without generating an air lock in metering chamber 60, and in particular lower cylindrical chamber 75. The area above valve 135 is vented to atmosphere via a small hole in cap 65.

As seen in FIG. 3, sealing lip 100 is structured to engage the interior of the wall of upper cylindrical chamber 70 when cap 65 is fully lowered. This seal prevents the liquid remaining in metering chamber 60 from leaking when metering device 25 is inverted.

Figure 6:
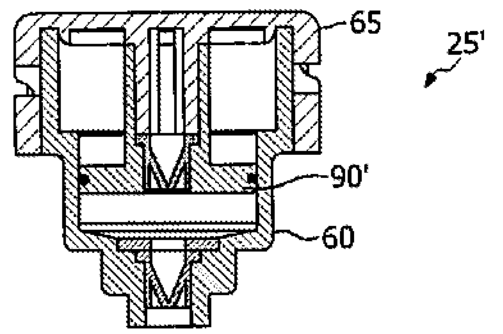
FIGS. 6 and 7 are cross-sectional views of metering devices according to alternative embodiments of the present invention.
Figure 7:
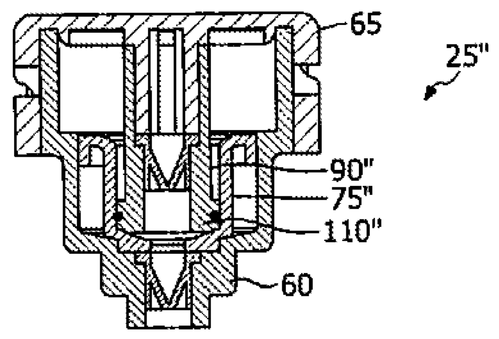

As will be appreciated, the dose volume of the liquid medication that is expelled from lower cylindrical chamber 75 and into reservoir 35 will be substantially determined by the bore of lower cylindrical chamber 75 and the stroke of piston 90. Thus, the dose volume may be controlled by controlling those features. FIG. 6 is a cross-sectional view of metering device 25' according to an alternative embodiment of the present invention having piston 90' having a reduced stroke as compared to piston 90. This will result in a smaller dose volume. FIG. 7 is a cross-sectional view of metering device 25" according to a further alternative embodiment of the present invention having lower cylindrical chamber 75", formed by a generally cylindrically shaped insert provided in metering chamber 60, having a reduced bore as compared to lower cylindrical chamber 75. In addition, metering device 25" includes piston 90" having bottom end 110" having a reduce diameter as compared to bottom end 110. This also will result in a smaller dose volume.

According to an aspect of the invention, nebulizer device 5 may be provided to the patient with multiple caps 65 each having a different piston 90, 90', and 90", and with one or more differently sized the inserts as shown in FIG. 7 so that the patient can selectively determine the dose of liquid that is metered by selecting a particular cap 65 and/or by using a particular insert. In one particular embodiment, the dimensions of the lower cylindrical chamber can be varied to meet the PRS of metered doses of 0.25 ml to 1.5 ml. The metering device as described herein in the various embodiments is able to meter doses with an accuracy of +−/10%, which is required under certain regulatory requirements.

Figure 8A:
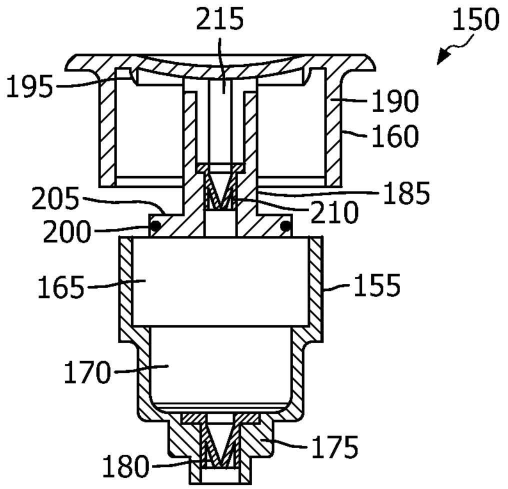
FIGS. 8A, 8B and 8C are cross-sectional views of a metering device according to another particular embodiment.
Figure 8B:
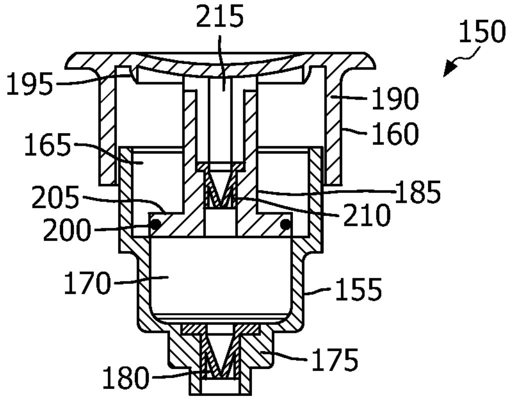
Figure 8C:
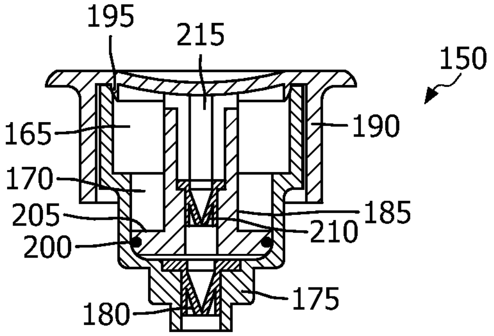

FIGS. 8A, 8B and 8C are cross-sectional views of metering device 150 according to an alternative embodiment. Metering device 150 includes metering chamber 155 and cap 160. Metering chamber 150 includes upper cylindrical chamber 165, lower cylindrical chamber 170, and port portion 175. As seen in FIGS. 8A to 8C, the bore (i.e., inner diameter) of upper cylindrical chamber 165 is larger that the bore (i.e., inner diameter) of lower cylindrical chamber 170. In an exemplary embodiment, metering chamber 155 is provided within main housing 10 of nebulizer 5 and metering device 150 is provided as an integral part of nebulizer 5. Alternatively, metering device 150 may be detachable and selectively coupled to reservoir 35. In either case, port portion 175 is structured to be in fluid communication with reservoir 35 and includes internal one-way valve 180, which in the embodiment shown is a rubber duck-bill valve. Cap 160 includes internal piston 185, outer wall 190 and sealing lip 195. Piston 185 is provided with sealing element 200, which in the illustrated embodiment is in the form of an O-ring, at cylindrical bottom end 205 of piston 185.

In operation, a vial containing liquid medication is emptied into metering chamber 155 where it fills both lower cylindrical chamber 170 and overflows into upper cylindrical chamber 165. The liquid medication is prevented from leaving the bottom of lower cylindrical chamber 170 by one-way valve 180. The volume of the liquid medication to be metered is substantially determined by the volume of lower cylindrical chamber 170 and the stroke of piston 185. Depending on the viscosity of the liquid it may also fill one-way valve 180. However the volume of space within the one-way valve 180 is small enough to not have a great effect on the overall dose tolerance. Cap 160 is then coupled to metering chamber 155 by inserting piston 185 into metering chamber 155 and pushing cap 160 downward. During this downward movement, seal element 200 engages with the inner wall surface of lower cylindrical chamber 170 and provides a seal and bottom end 205 of piston 185 is driven from the top to the bottom of lower cylindrical chamber 170. This movement delivers the metered volume of the liquid medication from lower cylindrical chamber 170 through port portion 175 and valve 180 (pressure from piston 185 causes valve 180 to open) to reservoir 35 of the mesh aerosol generation system of nebulizer 5 as described in more detail elsewhere herein. Any residual liquid will be contained in the lower cylindrical chamber 170 above bottom end 205 of piston 185 and the seal created by seal element 200.

Cap 160 may be removed by pulling upwardly on it. Piston 185 includes a central bore 215 having a second one-way valve 210, which in the illustrated embodiment is a rubber duck-bill valve, which allows cap 160 to be removed from metering chamber 155 without generating an air lock in metering chamber 155, and in particular lower cylindrical chamber 170. The area above valve 210 is vented to atmosphere via a small hole in cap 160. In addition, sealing lip 195 is structured to engage the interior of the wall of upper cylindrical chamber 165 when cap 160 is fully lowered. This seal prevents the liquid remaining in metering chamber 155 from leaking when metering device 150 is inverted.

Furthermore, the metering device as described herein in the various embodiments may also be designed so that it can only be used in specific nebulizers by keying the external shape of the metering chamber 60 to the device in which it is to be used.

While the present invention has been described in connection with a nebulizer, it should be understood that that is not meant to be limiting and that the present invention may be employed in connection with other types of medication delivery devices.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A medication delivery apparatus (5), comprising:

a reservoir (35) for holding a liquid medication; and a metering device (25, 150) coupled to the reservoir for supplying a dose of the liquid medication to the reservoir, the metering device including:

an upper chamber (70, 165) configured to receive liquid medication, the upper chamber including a first opening through which liquid medication is received into the upper chamber, and a second opening configured to communicate liquid medication out of the upper chamber, the first opening and the second opening formed along a longitudinal axis of the reservoir/upper chamber/delivery apparatus;

a lower chamber (75, 170) coupled to the upper chamber via the second opening such that liquid medication leaving the upper chamber is communicated to the lower chamber through the second opening;

a release opening configured to selectively release liquid medication from the lower chamber;

a piston (90, 185), the piston being selectively moveable within the upper chamber from the first opening toward the second opening and the lower chamber from the second opening toward the release opening along the longitudinal axis; and a valve (85, 180), the valve controlling selective release of the liquid medication through the release opening as the piston moves between the second opening of the upper chamber and the release opening of the lower chamber.

2. The medication delivery apparatus according to claim 1, wherein the valve is a one-way valve, wherein the valve is biased to be in a normally closed condition wherein the lower chamber is not in fluid communication with the reservoir and is structured to move to an open condition wherein the lower chamber is in fluid communication with the reservoir in response to a force being applied to the valve as a result of the piston moving toward the valve within the lower chamber.

3. The medication delivery apparatus according to claim 2, wherein the valve is a duck-bill valve.

4. The medication delivery apparatus according to claim 1, wherein the lower chamber and the upper chamber are each cylindrical in shape, and wherein a bore of the upper chamber is greater than a bore of the lower chamber.

5. The medication delivery apparatus according to claim 4, wherein the piston includes a cylindrical bottom end (110, 205) having a seal element (105, 200) coupled thereto, the seal element being structured to engage an inner wall of the lower chamber when the piston moves within the lower chamber.

6. The medication delivery apparatus according to claim 1, wherein the piston is part of a cap (65, 160) that is structured to be selectively coupled to the upper chamber.

7. The medication delivery apparatus according to claim 6, wherein when the cap is coupled to the upper chamber, the cap is structured to be rotatable relative to the upper chamber, and wherein rotation of the cap causes the piston to move within the lower chamber.

8. The medication delivery apparatus according to claim 7, wherein the upper chamber includes a pin (115) on an outer wall thereof, wherein the cap includes an angled thread (125), wherein the pin is structured to engage the thread when the cap is coupled to the upper chamber.

9. The medication delivery apparatus according to claim 8, wherein the thread is a quarter turn thread.

10. The medication delivery apparatus according to claim 6, wherein when the cap is coupled to the upper chamber, the cap is structured to be movable relative to the upper chamber along the longitudinal axis of the upper chamber, and wherein movement of the cap causes the piston to move within the lower chamber.

11. The medication delivery apparatus according to claim 6, wherein the piston includes a central bore (130, 215) and a second valve (135, 210) in the central bore, and wherein the central bore is vented to atmosphere through a hole provided in the cap.

12. The medication delivery apparatus according to claim 6, wherein the medication delivery apparatus further comprises one or more additional caps that may be selectively coupled to the upper chamber, each of the one or more additional caps having an associated piston that is different than the piston of the cap.

13. The medication delivery apparatus according to claim 12, wherein the piston of the cap has a first stroke, and wherein one or more of the one or more additional caps each having an associated piston having an associated stroke that is different than the first stroke.

14. The medication delivery apparatus according to claim 12, further comprising an insert structured to be received with the lower chamber, the lower chamber having a first bore and the insert having a second bore that is smaller than the first bore, wherein one of the one or more additional caps has an associated piston that is sized and structured for use with the insert.

15. The medication delivery apparatus according to claim 1, wherein the medication delivery apparatus is a nebulizer (5), wherein the reservoir is part of an aerosol generation system, and wherein the reservoir holds the dose of the liquid medication to enable the dose of the liquid medication to be nebulized by the aerosol generation system for delivery to a patient.

16. A method of providing a dose of a liquid medication to a reservoir (35) of a medication delivery apparatus (5), comprising:

supplying an amount of the liquid medication to an upper chamber (70, 165) and a lower chamber (75, 170) of a metering device (25, 150), the upper chamber comprising a first opening and a second opening, the lower chamber comprising a release opening, the amount of the liquid medication being larger than the dose, the lower chamber being coupled to the upper chamber at the second opening, a first portion of the amount being held in the lower chamber and a second portion of the amount being held in the upper chamber, wherein the lower chamber is not in fluid communication with the reservoir under a static pressure of the first portion in the lower chamber; and applying a force to the first portion in the lower chamber through the upper chamber, the force causing a piston to move from the second opening toward the release opening and force at least a part of the first portion to exit the lower chamber through the release opening and be received in the reservoir of the medication delivery apparatus, the second portion being maintained within the metering device after application of the force.

17. The method according to claim 16, wherein the applying the force includes applying the force by moving a piston (90, 185) within the upper chamber and the lower chamber.

18. The method according to claim 17, wherein the piston engages an inner wall of the lower chamber and provides a seal when the piston moves within the lower chamber.

19. The method according to claim 18, wherein the piston is part of a cap, wherein the applying a force further comprises coupling the cap to the upper chamber and moving the cap relative to the upper chamber along a longitudinal axis of the upper chamber.

20. The method according to claim 19, wherein the cap is one of a plurality of provided caps, wherein each one of the plurality of provided caps other than the cap has an associated piston having that is different than the piston of the cap, and wherein the method further comprises selecting the cap from among the number of provided caps.

21. The method according to claim 20, wherein the piston of the cap has a first stroke, and wherein each one or more of the plurality of provided caps other than the cap has an associated piston having an associated stroke that is different than the first stroke.

22. The method according to claim 20, further comprising creating the lower chamber by inserting an insert into a metering chamber of the metering device, the metering chamber including the upper chamber, wherein the piston of the cap is sized and structured for use with the insert.

23. The method according to claim 17, wherein the piston is part of a cap (65, 160), wherein the applying a force further comprises coupling the cap to the upper chamber and rotating the cap relative to the upper chamber, and wherein rotation of the cap causes the piston to move within the lower chamber.

24. The method according to claim 23, wherein the upper chamber includes a pin (115) on an outer wall thereof, wherein the cap includes an angled thread (125), wherein the coupling comprises causing the pin to engage the thread, and wherein the thread moves relative to the pin when the cap is rotated relative to the upper chamber.

25. The method according to claim 23, wherein rotation of the cap causes the piston to move within the lower chamber in a first direction, wherein the piston includes a central bore (130, 215), and wherein the method further includes venting the central bore to atmosphere as the piston is moved in a second direction opposite the first direction.

26. The method according to claim 16, wherein the metering device includes a valve (85, 180) providing selective fluid communication between the lower chamber and the reservoir, wherein the valve is biased in a normally closed condition under the static pressure wherein the lower chamber is not in fluid communication with the reservoir and wherein the applying a force causes the valve to move to an open condition wherein the lower chamber is in fluid communication with the reservoir.

* * * * *